(12) United States Patent
Wu et al.

(10) Patent No.: US 7,813,474 B2
(45) Date of Patent: Oct. 12, 2010

(54) METHOD AND APPARATUS FOR PERFORMING DUAL-SPECTRUM CT WITH FAST KV MODULATION AT MULTIPLE-VIEW INTERVALS

(75) Inventors: Xiaoye Wu, Rexford, NY (US); James W. LeBlanc, Niskayuna, NY (US); Paavana Sainath, Oconomowoc, WI (US); Thomas John Myers, Wauwatosa, WI (US); Charles Hugh Shaughnessy, Whitefish Bay, WI (US); Uwe Wiedmann, Buc (FR)

(73) Assignee: General Electric Company, Niskayuna, NY (US)

( * ) Notice: Subject to any disclaimer, the term of this patent is extended or adjusted under 35 U.S.C. 154(b) by 101 days.

(21) Appl. No.: 11/869,097

(22) Filed: Oct. 9, 2007

(65) Prior Publication Data

US 2009/0092219 A1 Apr. 9, 2009

(51) Int. Cl.
*H05G 1/60* (2006.01)
*H05G 1/32* (2006.01)
*A61B 6/03* (2006.01)

(52) U.S. Cl. ........................................ 378/16; 378/98.9

(58) Field of Classification Search .................. 378/16, 378/98.9
See application file for complete search history.

(56) References Cited

U.S. PATENT DOCUMENTS

| | | | | |
|---|---|---|---|---|
| 5,661,774 A | * | 8/1997 | Gordon et al. | 378/101 |
| 6,072,851 A | * | 6/2000 | Sivers | 378/15 |
| 6,922,462 B2 | * | 7/2005 | Acharya et al. | 378/98.11 |
| 7,209,537 B2 | * | 4/2007 | Popescu | 378/16 |

\* cited by examiner

*Primary Examiner*—Allen C. Ho
(74) *Attorney, Agent, or Firm*—Scott J. Asmus (57) ABSTRACT

A CT system includes a rotatable gantry having an opening for receiving a subject to be scanned, a rotatable gantry having an opening for receiving a subject to be scanned, an x-ray source configured to project x-rays having multiple energies toward the subject, and a generator configured to energize the x-ray source to a first voltage and configured to energize the x-ray source to a second voltage, the first voltage distinct from the second voltage. The system further includes a controller configured to cause the generator to energize the x-ray source to the first voltage for a first duration, acquire imaging data for at least one view during at least the first duration, after the first duration, cause the generator to energize the x-ray source to the second voltage for a second duration, and acquire imaging data for two or more views during at least the second duration.

20 Claims, 6 Drawing Sheets

METHOD AND APPARATUS FOR PERFORMING DUAL-SPECTRUM CT WITH FAST KV MODULATION AT MULTIPLE-VIEW INTERVALS

BACKGROUND OF THE INVENTION

The present invention relates generally to diagnostic imaging and, more particularly, to a method and apparatus of acquiring imaging data at more than one energy range using a multi-energy imaging source modulated at multiple-view intervals.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

A CT imaging system may include an energy discriminating (ED), multi energy (ME), and/or dual energy (DE) CT imaging system that may be referred to as an EDCT, MECT, and/or DE-CT imaging system. Such systems may use a scintillator or a direct conversion detector material in lieu of the scintillator. The EDCT, MECT, and/or DE-CT imaging system in an example is configured to be responsive to different x-ray spectra. For example, a conventional third generation CT system may acquire projections sequentially at different peak kilovoltage (kVp) levels, which changes the peak and spectrum of energy of the incident photons comprising the emitted x-ray beams. Energy sensitive detectors may be used such that each x-ray photon reaching the detector is recorded with its photon energy.

Techniques to obtain the measurements comprise: (1) scan with two distinctive energy spectra, and (2) detect photon energy according to energy deposition in the detector. EDCT/MECT/DE-CT provides energy discrimination and material characterization. For example, in the absence of object scatter, the system derives the behavior at a different energy based on the signal from two regions of photon energy in the spectrum: the low-energy and the high-energy portions of the incident x-ray spectrum. In a given energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two hypothetical materials.

A principle objective of dual energy scanning is to obtain diagnostic CT images that enhance contrast separation within the image by utilizing two scans at different chromatic energy states. A number of techniques have been proposed to achieve dual energy scanning including acquiring two scans either (1) back-to-back sequentially in time where the scans require two rotations around the subject, or (2) interleaved as a function of the rotation angle requiring one rotation around the subject, in which the tube operates at, for instance, 80 kVp and 140 kVp potentials. High frequency generators have made it possible to switch the kVp potential of the high frequency electromagnetic energy projection source on alternating views. As a result, data for two dual energy images may be obtained in a temporally interleaved fashion rather than two separate scans made several seconds apart as required with previous CT technology. Additionally, taking separate scans with several seconds apart from one another results in mis-registration between datasets caused by patient motion (both external patient motion and internal organ motion) and different cone angles. And, in general, a conventional two-pass dual kVp technique cannot be applied reliably where small details need to be resolved for body features that are in motion.

Therefore, it would be desirable to design an apparatus and method for acquiring imaging data at more than one energy state during a single scan having minimum patient motion and minimized cone angle effects.

BRIEF DESCRIPTION OF THE INVENTION

The present invention is a directed method and apparatus for acquiring imaging data at more than one energy state during a single scan.

According to an aspect of the present invention, a CT system includes a rotatable gantry having an opening for receiving a subject to be scanned, a rotatable gantry having an opening for receiving a subject to be scanned, an x-ray source configured to project x-rays having multiple energies toward the subject, and a generator configured to energize the x-ray source to a first voltage and configured to energize the x-ray source to a second voltage, the first voltage distinct from the second voltage. The system further includes a controller configured to cause the generator to energize the x-ray source to the first voltage for a first duration, acquire imaging data for at least one view during at least the first duration, after the first duration, cause the generator to energize the x-ray source to the second voltage for a second duration, and acquire imaging data for two or more views during at least the second duration.

According to another aspect of the present invention, a method of acquiring CT imaging data at more than one chromatic energy includes the steps of rotating an x-ray source mounted on a gantry about an object to be imaged, projecting a beam of x-ray energy having a first voltage toward the object during a first angular rotation of the gantry, and acquiring a first set of measured projections during the first angular rotation. The method further includes projecting a beam of x-ray energy having a second voltage toward the object during a second angular rotation of the gantry after acquiring the first set of measured projections, and acquiring a second set of two or more measured projections during the second angular rotation of the gantry.

According to yet another aspect of the present invention, a controller is configured to acquire imaging data at more than one chromatic energy state, the controller having instructions to energize an x-ray source mounted on a gantry, the energy source configured to project a first x-ray beam at a first voltage potential toward a subject to be scanned, acquire a first set of at least one view of data from the first x-ray beam, energize the x-ray source to a second voltage potential to project a second x-ray beam toward the subject, and acquire a second set of at least two subsequent views of data from the second x-ray beam.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise imaging, medical, security, and industrial inspection applications. However, it will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems.

The operating environment of the present invention is described with respect to a sixty-four-slice computed tomography (CT) system. However, it will be appreciated by those skilled in the art that the present invention is equally applicable for use with other multi-slice configurations.

Figure 1:
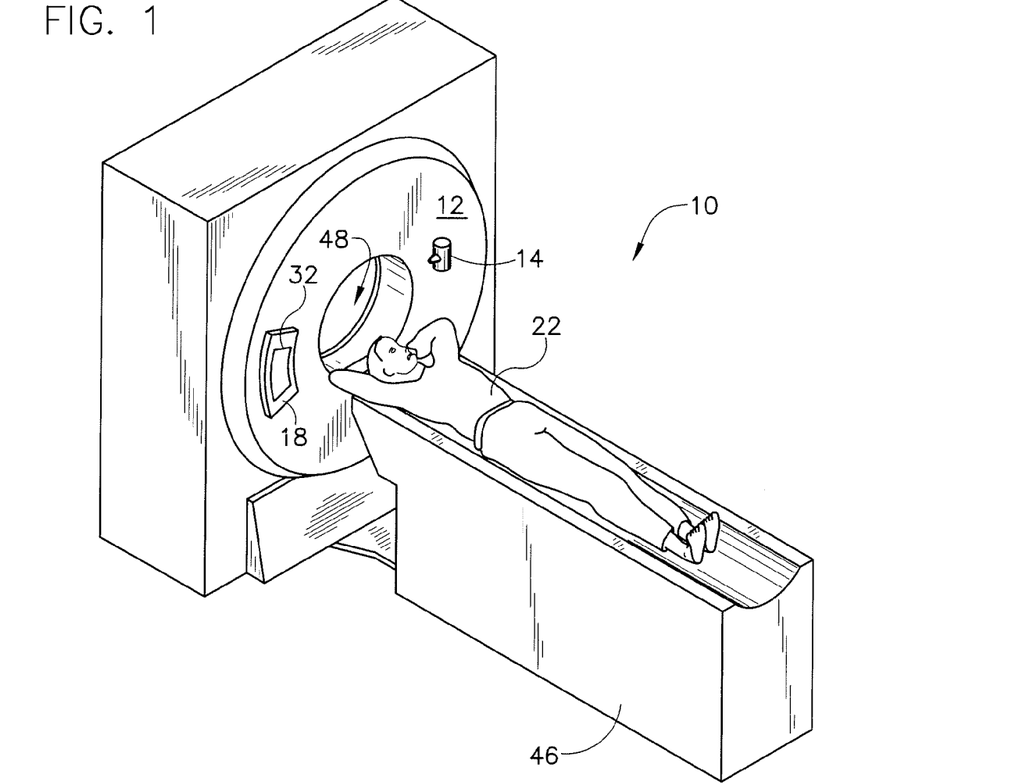
FIG. 1 is a pictorial view of a CT imaging system.
Figure 2:
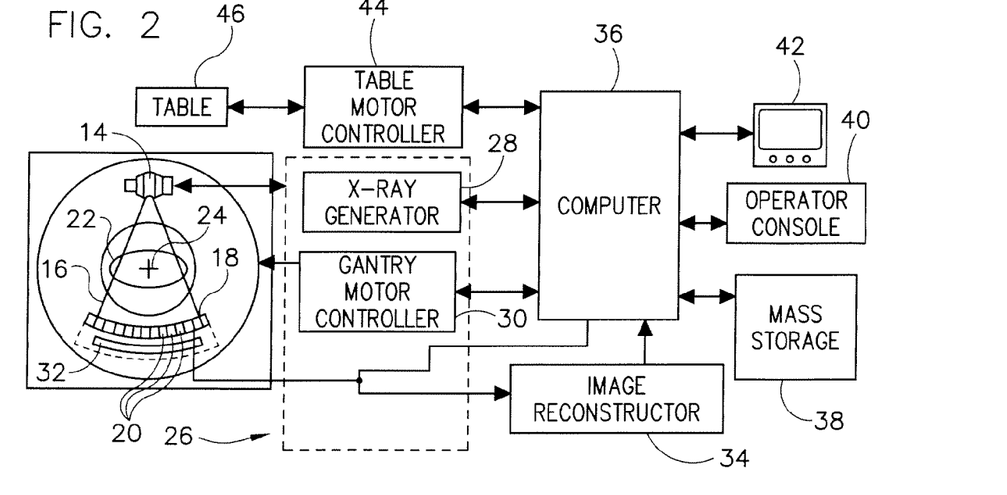
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a polychromatic beam of x-rays 16 toward a detector assembly 18 on the opposite side of the gantry 12. Typically, a collimator is an integral part of a detector assembly 18. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray generator 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray generator 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
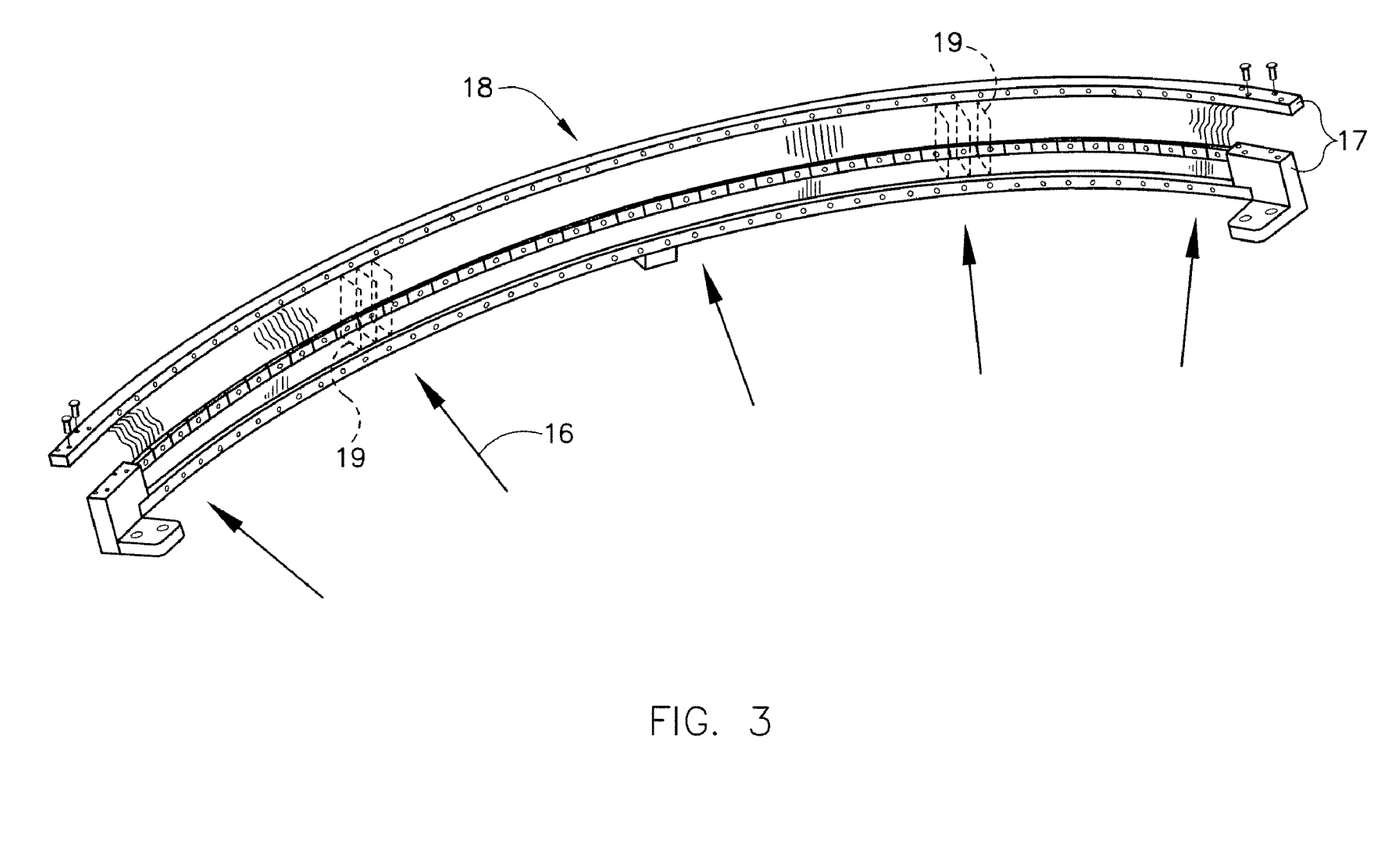
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
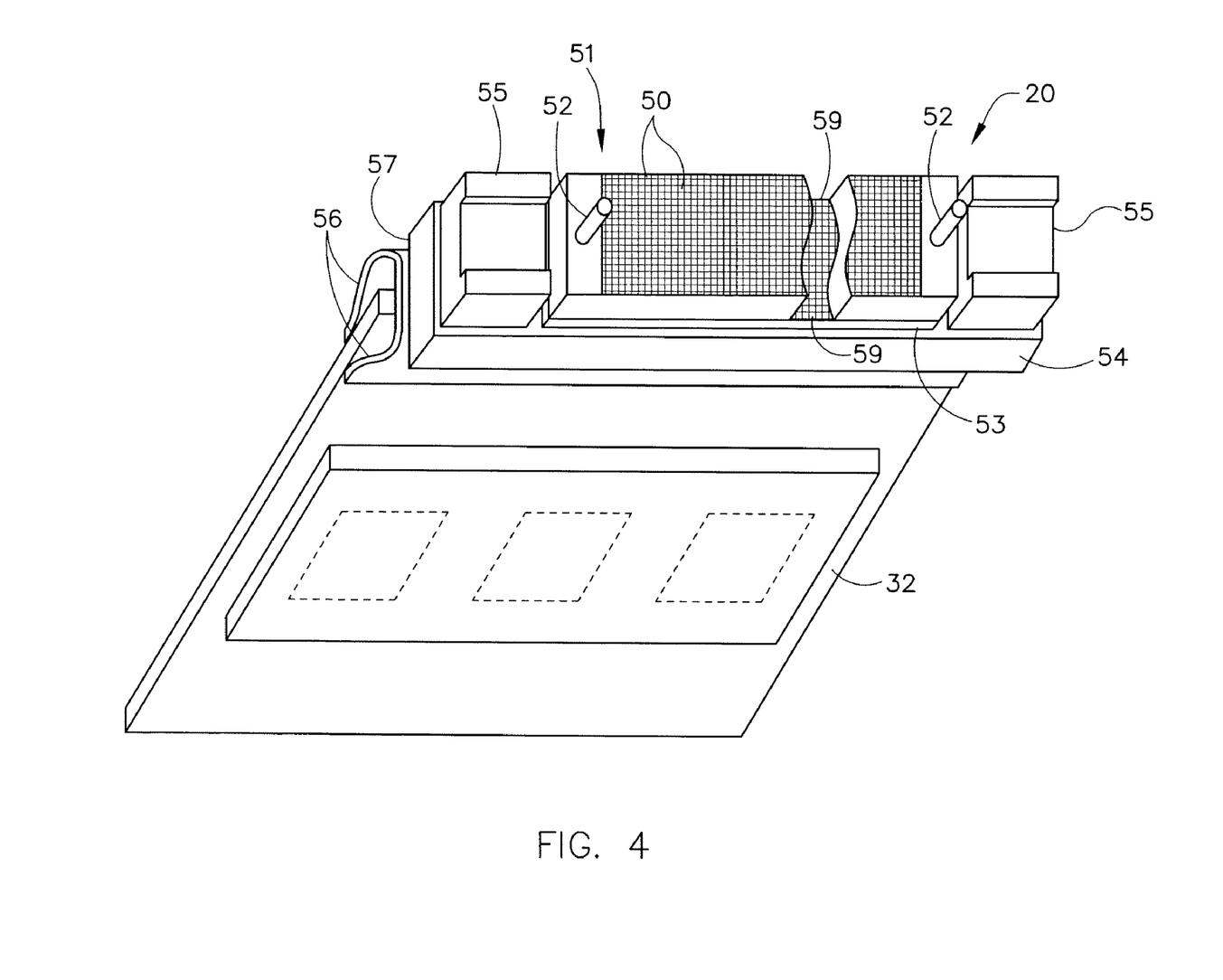
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

Figure 5:
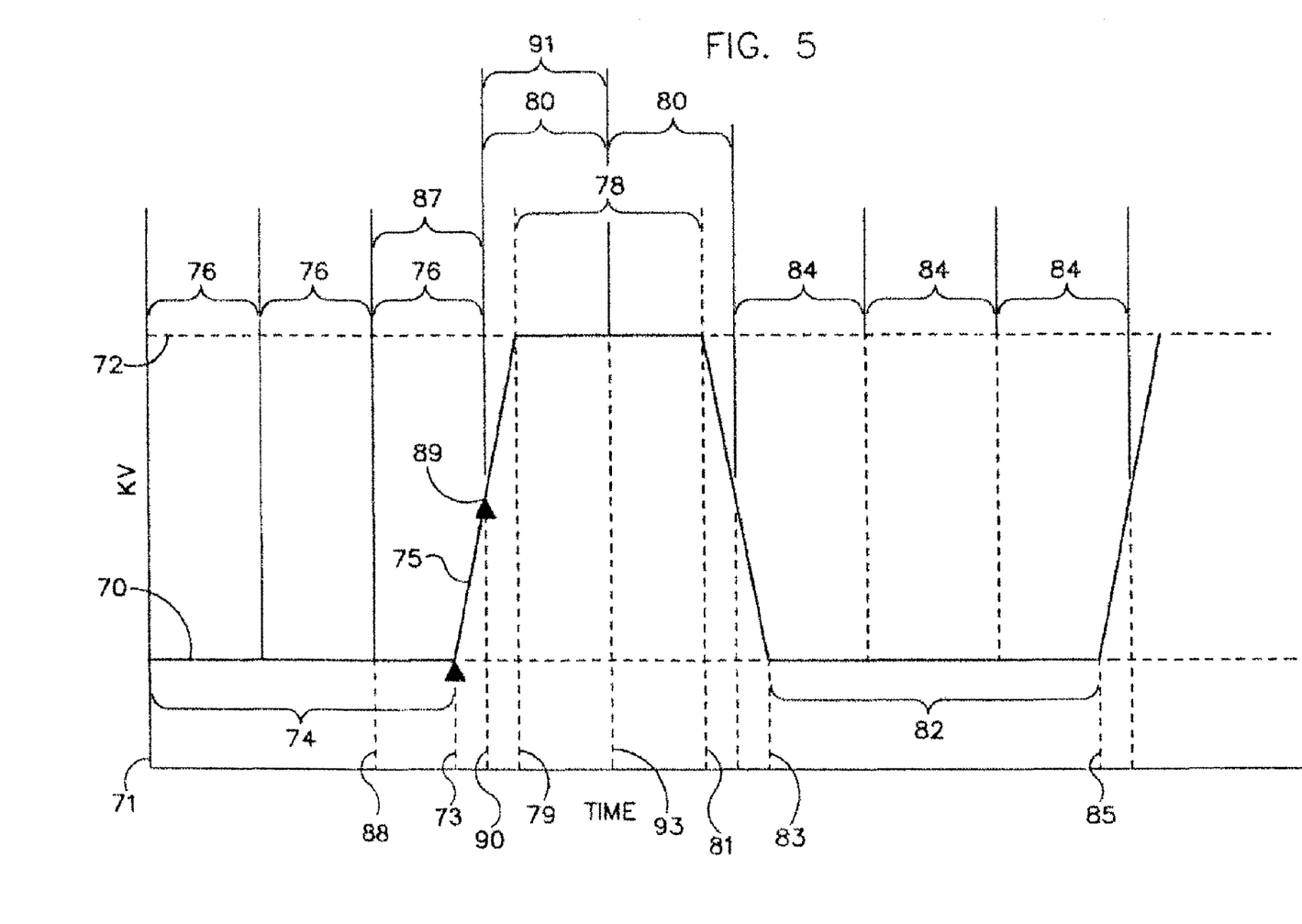
FIG. 5 is a plot of a low and high kVp protocol according to an embodiment of the present invention.

As discussed, conventional dual kVp CT scanning may be performed by, for instance, scanning first at one kVp and then at a second kVp. To overcome a possible mis-registration of the images acquired at the two kVps, a scanning sequence with dual kVp capability is illustrated in FIG. 5 according to an embodiment of the present invention. FIG. 5 shows that kVp modulation can be achieved in multiple-view intervals, such as every 0.3 to 2 msec, to greatly reduce or eliminate any mis-registration between the two kVp data sets, and at the same time provide sufficient data for image reconstruction at the two kVp's.

Referring now to FIG. 5, imaging data is acquired at a first voltage 70 and a second voltage 72 according to an embodiment of the present invention. Imaging data, in this and related embodiments, may also be referred to as views or as projections. In this embodiment, the x-ray generator 28 of FIG. 2, controlled by controller 26, provides the first voltage 70 to the x-ray tube 14 for a first duration 74, starting at or before a time 71 and providing the first voltage 70 until a time 73. During the first duration 74, one or more views 76 of data may be acquired by the computer 36 with the x-ray tube 14 at the first voltage 70. After the first duration 74, the x-ray generator 28 provides the second voltage 72 to the x-ray tube 14 for a second duration 78, starting at time 79 and providing the second voltage 72 until a time 81. During the second duration 78, two or more views 80 of data may be acquired by the computer 36 with the x-ray tube 14 at the second voltage 72. Thus as shown in FIG. 5, the number of views acquired during the first duration 74 and the second duration 78 are not equal or symmetric. For example, in one embodiment, m views are taken during the first duration and n views are taken during the second duration. After the second duration 78, the x-ray generator 28 may again be caused to supply the first voltage 70 to the x-ray tube 14 for a third duration 82, starting at time 83 and providing the first voltage 70 until a time 85. During the third duration 82, one or more views 84 of data may be acquired by the computer 36 with the x-ray tube 14 at the first voltage 70. In one embodiment of the present invention, the first voltage 70 is 80 kVp and the second voltage 72 is 140 kVp for x-ray tube 14. In another embodiment of the present invention, the electrical current of the x-ray tube 14 is controlled as a function of the applied voltages 70, 72.

Because of capacitive and other effects, the x-ray generator 28 is not capable of instantaneously switching from the first voltage 70 to the second voltage 72 and vice versa. As such, a finite time is typically required to allow for a voltage change to be achieved. For example, referring again to FIG. 5, the x-ray generator 28 may be at the first voltage 70 until time 73. At time 73, when the x-ray generator 28 is caused to output the second voltage 72, the output of the generator 28 will not achieve second voltage 72 until a later time 79. Thus, a transition time 75 occurs from time 73 to time 79 during which the x-ray generator 28 voltage is in transition between the two voltages 70, 72.

In order to avoid delaying an acquisition of view data at second voltage 72 after acquiring view data at first voltage 70 such that view data is acquired only when the second voltage 72 is actually achieved, view data may be acquired during the transition 75. In this manner, view data at first voltage 70 may be acquired in one portion of transition 75, and view data at second voltage 72 may be acquired in another portion of transition 75. As shown in FIG. 5, views 76 at first voltage 70 include a last view 87, which is started at time 88 and is ended at time 90 substantially corresponding to a point 89 of transition 75. Accordingly, view 87, in addition to including view data acquired at first voltage 70, includes view data acquired at voltages above first voltage 70 and below a voltage of point 89 between voltages 70, 72. Once the voltage of the x-ray tube 14 passes point 89, view 87 is complete, and acquisition of view data in a first view 91 of views 80 is begun. As such, the first view 91 is started at time 90 and is ended at time 93, which includes a voltage at second voltage 72.

Timing of signals in the x-ray generator 28 may be controlled by the computer 36 to minimize dose to the patient 22. Views 76 of data may be acquired at a first voltage 70, and a last view acquired 87 at the first voltage 70 may include data collected while the output voltage of the generator is in transition between voltages, that is, between time 73 and 90. Furthermore, a first view 91 of data including data acquired at the second voltage 72 may be triggered at time 90 to occur prior to the output voltage achieving the second voltage 72. In an embodiment of the present invention, the trigger point 89 as illustrated in FIG. 5 occurs substantially halfway between the first voltage 70 and the second voltage 72. However, one skilled in the art would recognize that the trigger may not be triggered at a point halfway between the two voltages 70, 72, but may be at some different point between the two voltages. One skilled in the art will also recognize that the pattern of low and high voltages may be repeated for different times and, accordingly, different gantry angles such that an interleaved pattern of data is acquired with one or more views obtained at the first voltage 70, two or more views obtained at the second voltage 72, and one or more views obtained again at the first voltage 70. One skilled in the art would further recognize that the number of views obtained during each duration need not be limited to the pattern as illustrated (i.e., three views at the first voltage 70, two views at the second voltage 72, and three views again at the first voltage 70), but may range from 2-50 views for a few tens of msec at each kVp before switching back to the other kVp.

In general, in using two projections $P_{low}$ and $P_{high}$ from the same angular position, one at a low kVp and another at a high kVp, material specific information can be obtained through a basis material decomposition process. In this process, x-ray attenuation coefficients of any material can be expressed as a weighted sum of two basis materials in an energy region where the materials do not have a k-edge in their attenuation curves. A machine specific material decomposition function f1( ) and f2( ) can be derived to obtain basis material density line-integrals from the measured x-ray attenuation at the high and low kVps, such as $\int d_{m1} dl = f_1(P_{low}, P_{high})$, and $\int d_{m2} dl = f_2(P_{low}, P_{high})$, where $d_{m1}$ and $d_{m2}$ are the densities of basis material 1 and 2 respectively. Using the material density line-integrals, CT reconstruction can yield density images of the two basis materials, which are quantitative, accurate and free of beam hardening. Thus, high and low kVp projection data must be obtained at the same gantry angle with no or very small time delay in between the two acquisitions.

Figure 6:
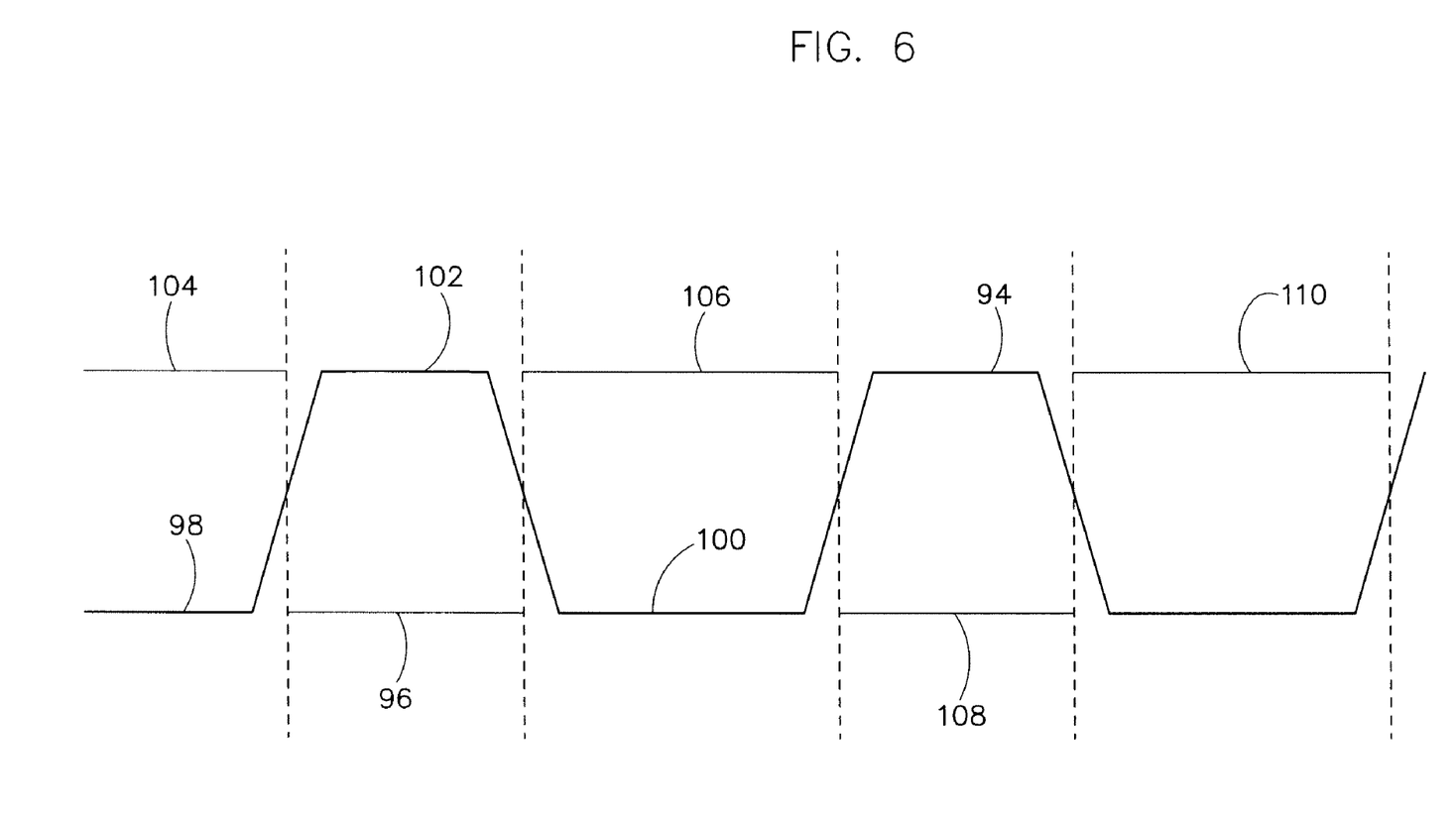
FIG. 6 is an interpolation method to illustrate generation of interpolated kVp data from measured kVp data according to an embodiment of the present invention.

Referring now to FIG. 6, measured projections at a given gantry angle may be obtained from neighboring views of data according to an embodiment of the present invention. As an example, and corresponding to the data as shown in FIG. 5, profile 94 includes measured projections obtained at high kVp, per the discussion related to FIG. 5. According to an embodiment of the present invention, measured projections at each voltage may be used to obtain corresponding interpolated projections as well, in order to provide basis material data for CT reconstruction as discussed above. For instance, low kVp projection data 96 may be obtained by interpolating neighboring measured projection data 98 and 100. As such, interpolated low kVp projection data 96 and measured high kVp projection data 102 provide data at the two kVps for a given gantry angle. The interpolation method described herein may be extended to other views. Thus interpolated data 104-110 may be obtained in likewise fashion by using neighboring measured projection data. As such, measured projection data provides not only measured data of interleaved high and low kVp data, it also forms the basis for interpolating corresponding data at given gantry angles, thus enabling high and low kVp projection data at equivalent times and providing views for performing a basis material decomposition.

Figure 7:
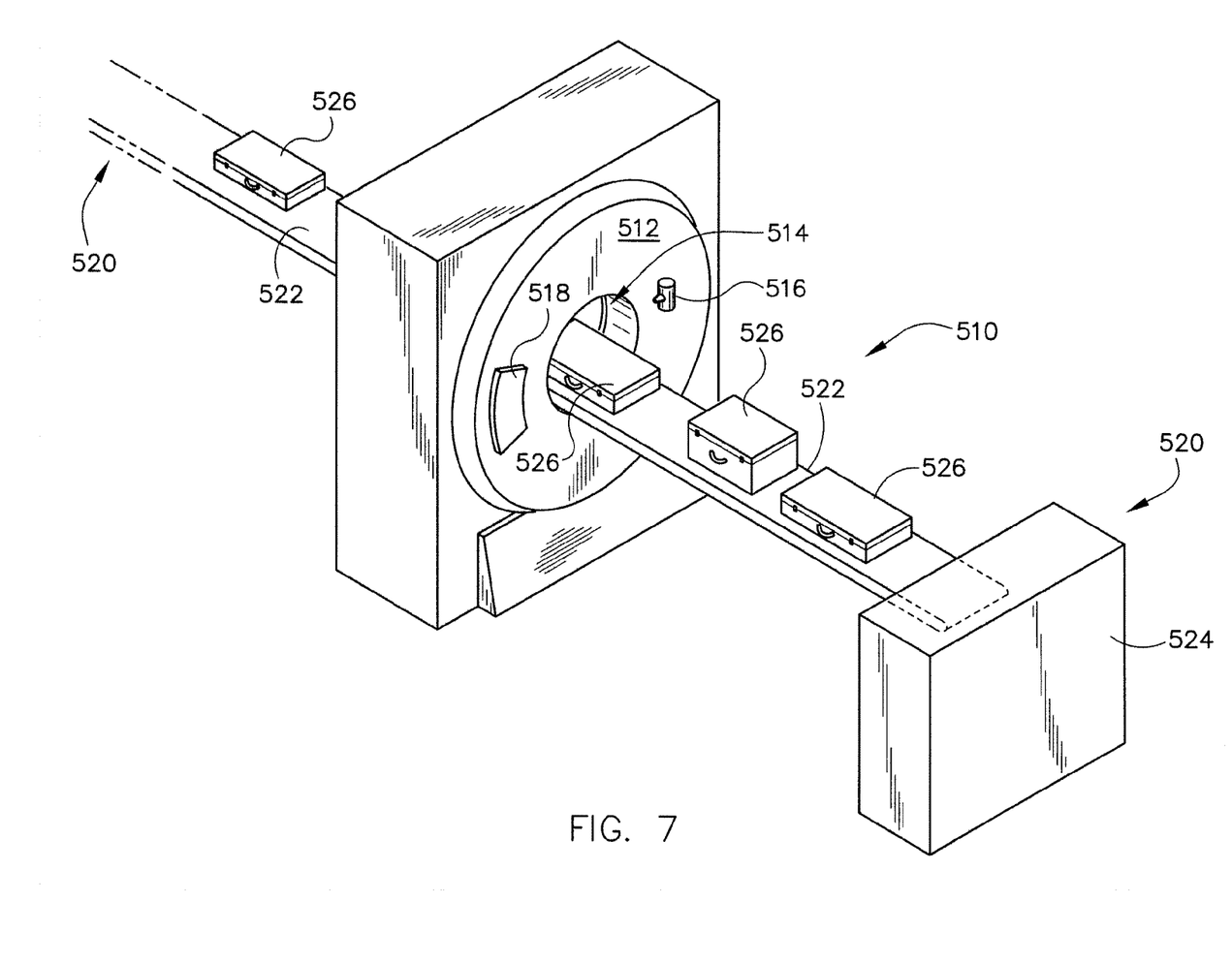
FIG. 7 is a pictorial view of a CT system for use with a non-invasive package inspection system according to an embodiment of the present invention.

Referring now to FIG. 7, package/baggage inspection system 510 includes a rotatable gantry 512 having an opening 514 therein through which packages or pieces of baggage may pass. The rotatable gantry 512 houses a high frequency electromagnetic energy source 516 as well as a detector assembly 518 having scintillator arrays comprised of scintillator cells similar to that shown in FIG. 4. A conveyor system 520 is also provided and includes a conveyor belt 522 supported by structure 524 to automatically and continuously pass packages or baggage pieces 526 through opening 514 to be scanned. Objects 526 are fed through opening 514 by conveyor belt 522, imaging data is then acquired, and the conveyor belt 522 removes the packages 526 from opening 514 in a controlled and continuous manner. As a result, postal inspectors, baggage handlers, and other security personnel may non-invasively inspect the contents of packages 526 for explosives, knives, guns, contraband, etc.

A technical contribution for the disclosed method and apparatus is that it provides for a computer implemented method of acquiring imaging data at more than one energy range using a multi-energy imaging source modulated at multiple-view intervals.

An implementation of the system 10 and/or 510 in an example comprises a plurality of components such as one or more of electronic components, hardware components, and/or computer software components. A number of such components can be combined or divided in an implementation of the system 10 and/or 510. An exemplary component of an implementation of the system 10 and/or 510 employs and/or comprises a set and/or series of computer instructions written in or implemented with any of a number of programming languages, as will be appreciated by those skilled in the art. An implementation of the system 10 and/or 510 in an example comprises any (e.g., horizontal, oblique, or vertical) orientation, with the description and figures herein illustrating an exemplary orientation of an implementation of the system 10 and/or 510, for explanatory purposes.

An implementation of the system 10 and/or the system 510 in an example employs one or more computer readable signal bearing media. A computer-readable signal-bearing medium in an example stores software, firmware and/or assembly language for performing one or more portions of one or more implementations. An example of a computer-readable signal bearing medium for an implementation of the system 10 and/or the system 510 comprises the recordable data storage medium of the image reconstructor 34, and/or the mass storage device 38 of the computer 36. A computer-readable signal-bearing medium for an implementation of the system 10 and/or the system 510 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 510, for instance, one or more of a telephone network, a local area network ("LAN"), a wide area network ("WAN"), the Internet, and/or a wireless network.

Therefore, according to an embodiment of the present invention, a CT system includes a rotatable gantry having an opening for receiving a subject to be scanned, a rotatable gantry having an opening for receiving a subject to be scanned, an x-ray source configured to project x-rays having multiple energies toward the subject, and a generator configured to energize the x-ray source to a first voltage and configured to energize the x-ray source to a second voltage, the first voltage distinct from the second voltage. The system further includes a controller configured to cause the generator to energize the x-ray source to the first voltage for a first duration, acquire imaging data for at least one view during at least the first duration, after the first duration, cause the generator to energize the x-ray source to the second voltage for a second duration, and acquire imaging data for two or more views during at least the second duration.

According to another embodiment of the present invention, a method of acquiring CT imaging data at more than one chromatic energy includes the steps of rotating an x-ray source mounted on a gantry about an object to be imaged, projecting a beam of x-ray energy having a first voltage toward the object during a first angular rotation of the gantry, and acquiring a first set of measured projections during the first angular rotation. The method further includes projecting a beam of x-ray energy having a second voltage toward the object during a second angular rotation of the gantry after acquiring the first set of measured projections, and acquiring a second set of two or more measured projections during the second angular rotation of the gantry.

According to yet another embodiment of the present invention, a controller is configured to acquire imaging data at more than one chromatic energy state, the controller having instructions to energize an x-ray source mounted on a gantry, the energy source configured to project a first x-ray beam at a first voltage potential toward a subject to be scanned, acquire a first set of at least one view of data from the first x-ray beam, energize the x-ray source to a second voltage potential to project a second x-ray beam toward the subject, and acquire a second set of at least two subsequent views of data from the second x-ray beam.

The present invention has been described in terms of the preferred embodiment, and it is recognized that equivalents, alternatives, and modifications, aside from those expressly stated, are possible and within the scope of the appending claims.

What is claimed is:

1. A CT system comprising:
    a rotatable gantry having an opening for receiving a subject to be scanned;
    an x-ray source configured to project x-rays having multiple energies toward the subject;
    a generator configured to energize the x-ray source to a first voltage and configured to energize the x-ray source to a second voltage, the first voltage distinct from the second voltage; and
    a controller configured to:
        cause the generator to energize the x-ray source to the first voltage for a first duration;
        acquire imaging data for a first number of views during the first duration;
        after the first duration, cause the generator to energize the x-ray source to the second voltage for a second duration;
        acquire imaging data for a second number of views during the second duration; and
    wherein the first number of views and the second number of views are not equal and the first duration and the second duration are not equal.

2. The CT system of claim 1 wherein the generator is further configured to:

output a first current when the generator is energized to the first voltage; and output a second current different from the first current when the generator is energized to the second voltage.

3. The CT system of claim 1 wherein the controller is further configured to:

cause the generator to repeat the energization of the x-ray source to the first voltage for a third duration after causing the generator to energize the x-ray source to the second voltage; and acquire imaging data for at least one view during at least the third duration.

4. The CT system of claim 3 wherein the second number of views measured at the second voltage have corresponding interpolated views at the first voltage, the interpolated views obtained by interpolating between the views measured at the first voltage during the first duration and the views measured at the first voltage during the third duration.

5. The CT system of claim 4 wherein the interpolation is a linear interpolation.

6. The CT system of claim 3 wherein the controller is configured to cause the energization and the repetition of the energization of the x-ray source to the first voltage via the generator within a single rotation of the gantry.

7. The CT system of claim 1 wherein the second voltage is greater in magnitude than the first voltage.

8. The CT system of claim 7 wherein the first voltage is approximately 80 kVp and the second voltage is approximately 140 kVp.

9. The CT system of claim 1 wherein the controller is further configured to delay acquiring image data for the second duration until an output voltage of the generator is between the first voltage and the second voltage.

10. The CT system of claim 9 wherein the delay is until the generator outputs a voltage approximately halfway between the first voltage and the second voltage.

11. A method of acquiring CT imaging data at more than one chromatic energy comprising the steps of:

rotating an x-ray source mounted on a gantry about an object to be imaged;

projecting a beam of x-ray energy having a first voltage toward the object during a first angular rotation of the gantry;

acquiring a first set of a first number of measured projections during the first angular rotation;

projecting a beam of x-ray energy having a second voltage toward the object during a second angular rotation of the gantry after acquiring the first set of measured projections;

acquiring a second set of a second number of measured projections during the second angular rotation of the gantry and wherein the first number of measured projections and the second number of measured projections are not equal.

12. The method of claim 11 further comprising:

projecting another beam of x-ray energy at the first voltage during a third angular rotation of the gantry after acquiring the second set of measured projections; and acquiring a third set of one or more measured projections at the first voltage during the third angular rotation of the gantry.

13. The method of claim 12 further comprising interpolating between the first set of measured projections and the third set of measured projections obtained at the first voltage to generate interpolated projections at the first voltage for gantry angles that correspond to measured projections acquired at the second voltage.

14. The method of claim 11 further comprising acquiring the first measured projection of the second set of measured projections while the x-ray energy is changing from the first voltage to the second voltage.

15. The method of claim 14 further comprising triggering the acquisition of the first measured projection of the second set of measured projections when the electromagnetic energy is approximately halfway between the first voltage and the second voltage.

16. A controller configured to acquire imaging data at more than one chromatic energy state, the controller having instructions to:

energize an x-ray source mounted on a gantry, the x-ray source configured to project a first x-ray beam at a first voltage potential toward a subject to be scanned;

acquire a first set of a first number of views of data from the first x-ray beam during a first angular rotation of the gantry;

energize the x-ray source to a second voltage potential to project a second x-ray beam toward the subject; and acquire a second set of a second number of views of data from the second x-ray beam during a second angular rotation of the gantry, wherein the first number of views and the second number of views are not equal.

17. The controller of claim 16 wherein the first voltage potential is approximately 80 kVp and the second voltage potential is approximately 140 kVp.

18. The controller of claim 16 further configured to:

energize the x-ray source to the first voltage potential to project a third x-ray beam toward the subject; and acquire a third set of one or more subsequent views of data therefrom.

19. The controller of claim 18 further configured to determine a set of projection data at the first voltage potential that corresponds to gantry angles of the second set of data, by interpolating between the first set and third set of data.

20. The controller of claim 16 further configured to begin acquiring the second set of data while the x-ray source is transitioning between the first voltage potential and the second voltage potential.

* * * * *